US012366536B2

United States Patent
Noumi et al.

(10) Patent No.: US 12,366,536 B2
(45) Date of Patent: Jul. 22, 2025

(54) METHOD OF INSPECTING JOINT PORTION OF FLUORORESIN MEMBER AND FLUORORESIN MEMBER INSPECTION METHOD

(71) Applicant: DAIKIN INDUSTRIES, LTD., Osaka (JP)

(72) Inventors: Masao Noumi, Osaka (JP); Atsushi Sakakura, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 315 days.

(21) Appl. No.: 17/726,646

(22) Filed: Apr. 22, 2022

(65) Prior Publication Data
US 2022/0244191 A1    Aug. 4, 2022

Related U.S. Application Data (63) Continuation of application No. PCT/JP2020/038256, filed on Oct. 9, 2020.

(30) Foreign Application Priority Data

Oct. 30, 2019    (JP) ................. 2019-197731

(51) Int. Cl.
*G01N 21/88*    (2006.01)
*G01N 21/95*    (2006.01)

(52) U.S. Cl.
CPC ......... *G01N 21/8851* (2013.01); *G01N 21/95* (2013.01); *G01N 2021/8887* (2013.01)

(58) Field of Classification Search
CPC .............. G01N 21/8851; G01N 21/95; G01N 2021/8887
See application file for complete search history.

(56) References Cited

U.S. PATENT DOCUMENTS

2012/0320380 A1* 12/2012 Schonleber ........ G01B 9/02044
356/479

FOREIGN PATENT DOCUMENTS

| EP | 1 125 731 A1 | 8/2001 | |
| EP | 3 940 374 A1 | 1/2022 | |
| JP | 2006-145559 A | 6/2006 | |
| WO | WO-2004052627 A1 * | 6/2004 | ............. B29C 65/10 |
| WO | 2019/025011 A1 | 2/2019 | |

OTHER PUBLICATIONS

"State-of-the-art Nondestructive Technology for Composite Material", Mitsubishi Heavy Industries Technical Review vol. 54 No. 4 (Dec. 2017) by Uematsu et al. (Year: 2017).*

(Continued)

*Primary Examiner* — Jamil Ahmed
(74) *Attorney, Agent, or Firm* — Sughrue Mion, PLLC (57) ABSTRACT

A method for inspecting a joint portion between fluororesin members, including: a step (A1) of inspecting an internal condition of a joint portion between a fluororesin member (A1) and a fluororesin member (A2) based on image data obtained by imaging the joint portion by optical coherence tomography. Also disclosed is a method for inspecting a fluororesin member, including: a step (B1) of inspecting a defect inside a fluororesin member (B1) based on image data obtained by imaging the fluororesin member (B1) by optical coherence tomography.

6 Claims, 4 Drawing Sheets

(56) References Cited

OTHER PUBLICATIONS

Mitsuyoshi Uematsu et al., "State-of-the-art Nondestructive Inspection Technology for Composite Materials", Mitsubishi Heavy Industries Technical Review, 2017, pp. 24-28, vol. 54 No. 4.
Bing Wu et al., "Optimization of gravity-driven membrane (GDM) filtration process for seawater pretreatment", Water Research, 2016, pp. 133-140, vol. 93.
International Search Report of PCT/JP2020/038256 dated Dec. 8, 2020 [PCT/ISA/210].
International Preliminary Report on Patentability dated May 3, 2022 with a Translation of the Written Opinion of the International Searching Authority in Application No. PCT/JP2020/038256.
Karin Wiesauer, et al., Investigation of glass-fibre reinforced polymers by polarisation-sensitive, ultra-high resolution optical coherence tomography: Internal structures, defects and stress, Elsevier, Composites Science and Technology, vol. 67, 2007, pp. 3051-3058 (8 pages).
Qi Han, et al., "Assessing internal fouling during microfiltration using optical coherence tomography and evapoporometry", Elsevier, Journal of Membrane Science, vol. 595 , 2020 (13 pages).
Extended European Search Report dated Oct. 23, 2023 in counterpart Application No. 20880967.3.
Yonghong Shao et al.; "Research of a Novel Method to Inspecting Engineering Polymer"; Laser & Infrared; vol. 36, No. 9; Sep. 2006.

\* cited by examiner

METHOD OF INSPECTING JOINT PORTION OF FLUORORESIN MEMBER AND FLUORORESIN MEMBER INSPECTION METHOD

CROSS REFERENCE TO RELATED APPLICATIONS

This application is a Rule 53(b) Continuation of International Application No. PCT/JP2020/038256 filed on Oct. 9, 2020, claiming priority based on Japanese Patent Application No. 2019-197731 filed on Oct. 30, 2019, the respective disclosures of which are incorporated herein by reference in their entirety.

TECHNICAL FIELD

The disclosure relates to methods for inspecting a joint portion between fluororesin members and methods for inspecting a fluororesin member.

BACKGROUND ART

Fluororesin is excellent in properties such as heat resistance, abrasion resistance, and chemical resistance and is widely used, as one of representative engineering plastics, for products such as molded articles.

Patent Literature 1 discloses a specific method for ultrasonically inspecting an object to be inspected made from a fluororesin.

CITATION LIST

Patent Literature

Patent Literature 1: JP 2006-145559 A

SUMMARY

The disclosure relates to a method for inspecting a joint portion between fluororesin members, including: a step (A1) of inspecting an internal condition of a joint portion between a fluororesin member (A1) and a fluororesin member (A2) based on image data obtained by imaging the joint portion by optical coherence tomography.

Advantageous Effects

The disclosure can provide a novel inspection method enabling non-destructive inspection of an internal condition of a joint portion between fluororesin members or an internal condition of a fluororesin member.

DESCRIPTION OF EMBODIMENTS

The disclosure is specifically described below.

The disclosure relates to a method for inspecting a joint portion between fluororesin members, including a step (A1) of inspecting an internal condition of a joint portion between a fluororesin member (A1) and a fluororesin member (A2) based on image data obtained by imaging the joint portion by the optical coherence tomography (OCT) (hereafter, also referred to as a first inspection method).

The first inspection method enables non-destructive inspection of an internal condition of a joint portion between fluororesin members, and thus enables inspection of all joint portions. This can therefore improve the reliability of the quality of joined bodies including the joint portion.

The first inspection method enables precise analysis based on the obtained image data, and thus enables detection of defects including minor internal defects and digitalization of the condition of a joint interface. This enables exact understanding of the internal condition of the joint portion, allowing determination of an objective index for examining the quality of the joint portion. Thus, the quality of the joined bodies can be stabilized.

OCT imaging can be performed at high speed, and thus the inspection method can be easily introduced into a working site where fluororesin members are joined. This enables improvement and stabilization of the quality of the joined bodies without greatly increasing the number of steps carried out at the working site.

In the step (A1), the joint portion between the fluororesin member (A1) and the fluororesin member (A2) is to be inspected. The joint portion may be a joint portion between the fluororesin member (A1) and the fluororesin member (A2) in a joined body in which the fluororesin member (A1) and the fluororesin member (A2) are joined together.

The term "join/joint" herein refers to joining of objects to such an extent that they cannot be separated except by mechanical cutting or a state where objects are joined together in that way.

The fluororesin members (A1) and (A2) may have the same or different features including shape and size.

The fluororesin members (A1) and (A2) may be different members or different parts in the same member.

The numbers of the fluororesin members (A1) and (A2) are not limited, and each may be one or more.

The fluororesin members (A1) and (A2) are members containing a fluororesin.

The fluororesin members (A1) and (A2) preferably contain different fluororesins.

The interface between different fluororesins is likely to have internal defects such as delamination and cracking.

The first inspection method enables detecting the presence of such internal defects.

The fluororesin members (A1) and (A2) each may be a molded article or a joint member. The fluororesin members (A1) and (A2) may be a combination of a molded article and a joint member. The joint member herein refers to a member for joining multiple different members.

According to a preferred embodiment, at least one of the fluororesin members (A1) and (A2) includes a sheet containing a fluororesin. According to another preferred embodiment, each of the fluororesin members (A1) and (A2) includes the sheet.

According to a preferred embodiment, at least one of the fluororesin members (A1) and (A2) includes a laminate that includes a sheet containing a fluororesin and a heat-resistant fiber layer. According to another preferred embodiment, each of the fluororesin members (A1) and (A2) includes the laminate.

Descriptions are later given on the fluororesin contained in the fluororesin members (A1) and (A2), the molded article, the joint member, the sheet, and the laminate.

In the case where the fluororesin members (A1) and (A2) are sheet-shaped members, they may be joined in the thickness direction or in the plane direction (direction perpendicular to the thickness direction).

The fluororesin member (A1) and the fluororesin member (A2) are preferably fused at the joint portion.

Exemplary joining embodiments of the fluororesin members (A1) and (A2) are described based on drawings. The joining embodiments in the disclosure are not intended to be limited to these examples.

Figure 1:
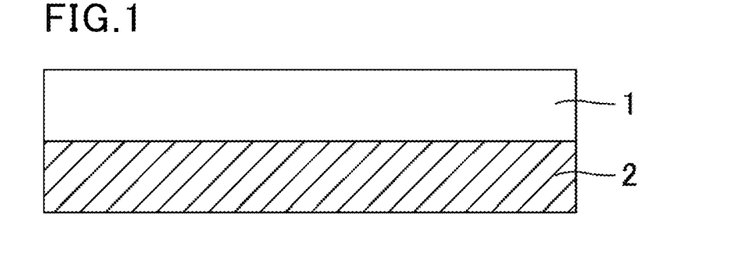
FIG. 1 is a schematic view of an example of a joining embodiment of fluororesin members.

In the embodiment in FIG. 1, a sheet 1 containing a fluororesin and a sheet 2 containing a fluororesin are joined together in the thickness direction.

In this embodiment, the sheet 1 corresponds to the fluororesin member (A1) and the sheet 2 corresponds to the fluororesin member (A2), for example.

Figure 2A:
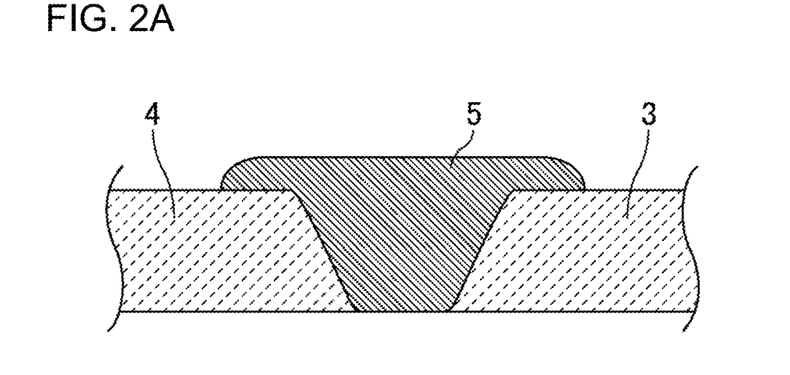
FIG. 2A and FIG. 2B are schematic views of other examples of the joining embodiment of fluororesin members.

In the embodiment in FIG. 2A, a sheet 3 containing a fluororesin is joined to a joint member 5 containing a fluororesin, and the joint member 5 is joined to a sheet 4 containing a fluororesin. In other words, the sheet 3 and the sheet 4 are joined together in the plane direction via the joint member 5.

Figure 2B:
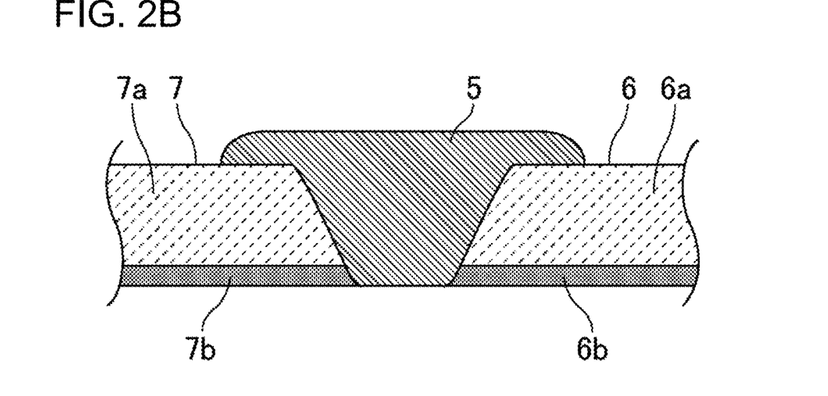

In the embodiment in FIG. 2B, a laminate 6 including a sheet 6a containing a fluororesin and a heat-resistant fiber layer 6b is joined to a joint member 5 containing a fluororesin, and the joint member 5 is joined to a laminate 7 including a sheet 7a containing a fluororesin and a heat-resistant fiber layer 7b. In other words, the laminate 6 and the laminate 7 are joined together in the plane direction via the joint member 5.

In these embodiments, the sheet 3, the sheet 4, the laminate 6, and the laminate 7 each correspond to the fluororesin member (A1) and the joint member 5 corresponds to the fluororesin member (A2), for example.

Joining may be performed by any conventionally known method.

In an exemplary method, the fluororesin members (A1) and (A2) are stacked and heated to a temperature not lower than the melting point of the fluororesin contained in at least one of the fluororesin members (A1) and (A2) optionally under pressurization. This method is suitably employed for the embodiment in FIG. 1, for example.

In another exemplary method, two or more fluororesin members (A1) are butted together with the fluororesin member (A2) interposed between them as a joint member, and they are heated to a temperature not lower than the melting point of the fluororesin contained in at least one of the fluororesin members (A1) and (A2) optionally under pressurization. In this method, the fluororesin members (A1) are each joined to the fluororesin member (A2) (two or more fluororesin members (A1) are joined together via the fluororesin member (A2)). This method is suitably employed for the embodiment in FIG. 2A and FIG. 2B, for example.

In the above method, at least one of the fluororesin members (A1) may have an inclination (beveling) at a portion to be joined.

In the above embodiment, two or more fluororesin members (A1) are preferably welded via the fluororesin member (A2).

The inspection in the step (A1) is performed based on image data obtained by imaging the joint portion by OCT. The first inspection method may include a step of imaging the joint portion by OCT to obtain image data based on the joint portion.

OCT is classified into time domain OCT (TD-OCT) and Fourier domain OCT (FD-OCT), and FD-OCT is further classified into spectral domain OCT (SD-OCT) and swept source OCT (SS-OCT).

Any OCT may be used in the step (A1), and SS-OCT is preferred owing to its high sensitivity and deep measurable depth.

Examples of light used for OCT include visible light and infrared light, and near-infrared (NIR) light is preferred.

In many cases of inspecting a fluororesin member composed of CF and CC bonds, light within almost the entire near-infrared wavelength range can be used. For a smaller crystal size, light on the long wavelength side of the visible region (600 nm or longer) and light on the short wavelength side of the infrared region (5000 nm or shorter) can also be used.

Preferred is light at a wavelength of 800 to 2000 nm because an applicable OCT device is easily available. In particular, light having a center wavelength of 940±50 nm, 1100±50 nm, 1320±50 nm, and 1750±100 nm are more preferred in terms of light source stability and sensor reliability.

Figure 3:
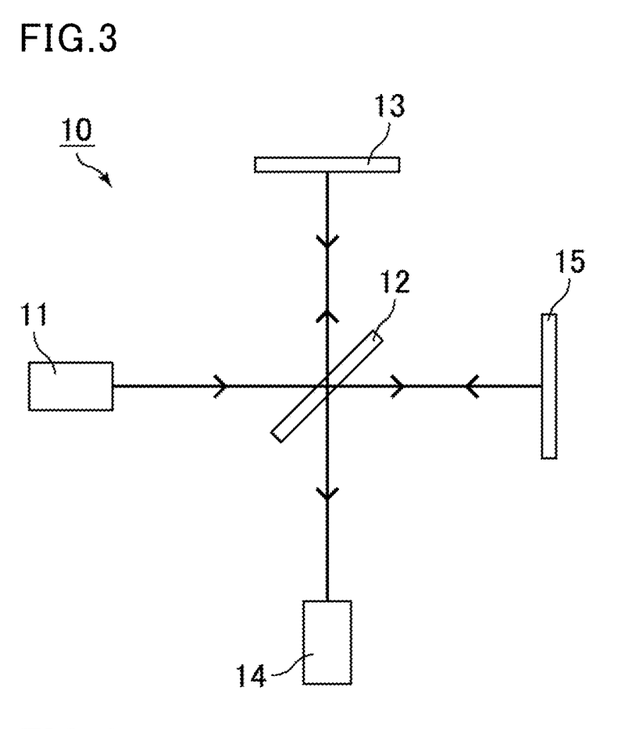
FIG. 3 is a schematic view of an example of an optical coherence tomography (OCT) device that may be used in the inspection method of the disclosure.

An example of an imaging method using an OCT device is described with reference to FIG. 3.

In an OCT device 10, light emitted from a light source 11 is separated into two beams by a beam splitter 12. One beam is reflected on a reference mirror 13 and then incident on a photodetector 14 as reference light. The other beam is incident on a sample (joined body) 15, permeates into a certain depth, and is reflected on the surface of the sample 15 or an internal defect such as cracking or delamination. The light reflected on the sample 15 passes through the beam splitter 12 and is incident on the photodetector 14 as signal light. The photodetector 14 detects interference light generated by interference between the reference light and the signal light, converts the interference light into a signal, and outputs the signal. This output signal is imaged in accordance with characteristics such as intensity, which can provide an image showing the structure of the sample 15.

The OCT device and imaging method that can be used in the inspection method of the disclosure are not limited to those described above.

In the OCT imaging, the light from the light source of an OCT device preferably has an incident angle α of 3 to 30 degrees relative to the joint portion. The incident angle α is more preferably 5 degrees or greater, still more preferably 7 degrees or greater, while more preferably 30 degrees or smaller, still more preferably 20 degrees or smaller, further more preferably 15 degrees or smaller, particularly preferably 10 degrees or smaller.

Setting the incident angle α within the above range can reduce noise in the image and can clarify a signal due to a defect of the joint portion.

The above effects are significant when the joint portion has a high near-infrared transmittance and when the front surface (surface close to the OCT light source) and back surface (surface opposite to the front surface) to be inspected of the joint portion are parallel to each other.

The incident angle α is defined as the angle formed by the incident direction of the light and a perpendicular to a surface of the joint portion. The surface may be the surface close to the OCT light source.

Figure 4:
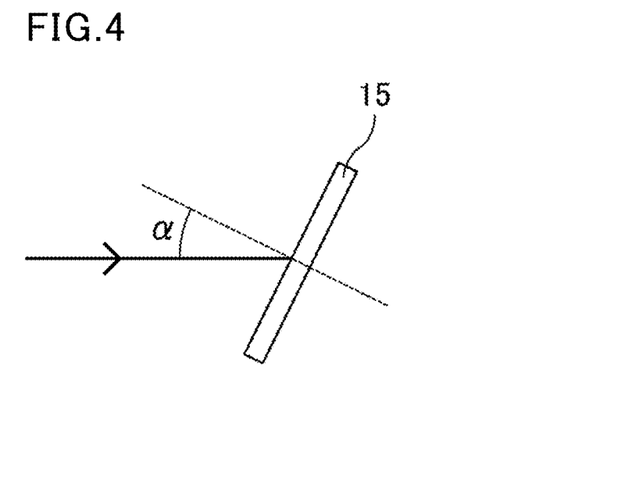
FIG. 4 is an enlarged view of an OCT device that may be used in the inspection method of the disclosure, showing an example of an embodiment in which a sample is placed with an inclination.

FIG. 4 shows an example of an embodiment in which a sample is placed with an inclination. In FIG. 4, light is incident on the sample 15 at an incident angle α.

The incident angle α can be adjusted, for example, by adjusting the inclination of a sample stage on which an object to be inspected (sample) is placed.

If one object to be inspected has two or more portions to be inspected, a plurality of OCT optical systems may be prepared and the portions to be inspected may be subjected to measurement simultaneously or sequentially. This is preferred because the incident angle α and an angle § can be adjusted to fall within the above respective preferred ranges even when the portions of the object to be inspected have different inclinations. This is also preferred because the OCT devices need no change in the specifications even when the portions to be inspected are apart from each other. This is also preferred because the incident angle α and the angle β can be adjusted correspondingly to the respective portions even when the portions of the object to be inspected form a large step therebetween.

In the OCT imaging, the light incident on the joint portion preferably has an intensity of 1 mW to 18 mW. The intensity of the light is more preferably 5 mW or higher, still more preferably 10 mW or higher, while more preferably 15 mW or lower, still more preferably 12 mW or lower.

Setting the intensity of the light within the above range can reduce noise in the image and can clarify a signal due to a defect of the joint portion.

The above effect is significant when the joint portion has a high near-infrared transmittance and when the front surface and back surface of the joint portion are parallel to each other.

In the description, the intensity of light incident on the joint portion is the intensity of light at a probe end of an OCT device.

When a portion to be inspected in the sample is close to a sample stage, reflection of light passed through the sample on the stage may cause noise. Thus, the system is preferably devised so that the light passed through the sample does not affect the inspection.

For example, an object that reflects light passed through a sample may be apart from a portion to be inspected of the sample by 10 mm or more. In this case, preferably, a portion not to be inspected (e.g., both ends of the sample) is used to support the sample so that the portion to be inspected and the sample stage do not overlap.

Alternatively, light passed through a sample may be reflected in a direction not oriented to the probe.

Still alternatively, an object that absorbs or scatters almost the entire light passed through a sample may be placed at a position where this light hits.

The above techniques may be used in combination as appropriate.

In the step (A1), an internal condition of the joint portion is inspected based on the image data.

The inspection may be performed using an image obtained from the image data or may be performed by processing the image data, or both may be used in combination.

In the step (A1), a condition of the interface between the fluororesin member (A1) and the fluororesin member (A2) inside the joint portion is preferably inspected.

In the case where one of the fluororesin members (A1) and (A2) is the laminate and the other is the joint member, inspection can be also performed on conditions of the interface between the sheet containing a fluororesin and the joint member, the interface between the heat-resistant fiber layer and the joint member, and the interface between the sheet containing a fluororesin and the heat-resistant fiber layer.

There may be a case where the fluororesin members (A1) and (A2) are mutually fused to form a layer at the interface of the fluororesin members (A1) and (A2). The above inspection can determine the presence or absence of such a mutually fused layer and the thickness of the layer, if present.

When at least one of the fluororesin members (A1) and (A2) is the laminate, there may be a case where a fired layer and an unfired layer are formed in the sheet containing a fluororesin as described later. The above inspection can determine the presence or absence of the fired layer and the unfired layer and the thicknesses of the layers, if present.

In the case where the laminate further includes a hot-melt resin layer described later, the above inspection can determine the presence or absence of a layer made of the heat-resistant fibers impregnated with a hot-melt resin and the thickness of the layer, if present.

The inspection is preferably inspection of a defect inside the joint portion.

Examples of the defect include cracking, delamination, voids, and foreign substances. Embodiments of the defect include the absence of a layer which should be present and the thickness of a layer not within a required range. The defect may be caused by joining (welding) failure or molding failure.

At the joint portion, the interface between different materials is likely to suffer denaturation or have voids, causing a defect.

The inspection preferably determines the presence or absence of a defect.

The step (A1) is preferably a step of inspecting a defect inside the joint portion based on the image data, more preferably a step of inspecting cracking and delamination inside the joint portion based on the image data.

The inspection may be performed based on a signal due to a defect inside the joint portion in the image data. Further, the presence or absence of a defect is preferably determined based on a signal due to the defect.

An example of a method for determining the presence or absence of the defect may be a method in which the cases where no signal due to any of the aforementioned defects is observed in the image obtained by the OCT are determined as the absence of a defect, while the cases where a signal due to at least one of the aforementioned defects is observed in the image are determined as the presence of a defect.

If the inspection determines the presence of a defect, the size, shape, orientation, occurrence frequency, and other properties of the defect may be further analyzed. Such analysis enables easy determination of whether or not the above defect is a defect that causes the joining condition of the joint portion to be determined as defective. The analysis may be performed, for example, by processing a signal due to the defect.

The inspection method of the disclosure may further include a step (A2) of determining whether the joining condition of the fluororesin members (A1) and (A2) in the joint portion is good or not based on a result of the inspection in the step (A1).

For example, the step (A2) may be a step of determining the joining condition as good when the case has been determined as the absence of a defect in the step (A1), while determining the joining condition as poor when the case has been determined as the presence of a defect in the step (A1).

Alternatively, the step (A2) may be a step of determining the joining condition as good when the case has been determined as the absence of a defect in the step (A1) and when the case has been determined as the presence of a defect in the step (A1) and the defect has a degree of defectiveness not higher than a predetermined standard, while determining the joining condition as poor when the case has been determined as the presence of a defect in the step (A1) and the defect has a degree of defectiveness higher than the predetermined standard.

The standard for the degree of defectiveness may be determined as appropriate with no limitation in accordance with, for example, the required characteristics of a joined body including the joint portion. For example, the standard may be determined by obtaining in advance a correlation between the properties of a defect such as the size, shape, orientation, and occurrence frequency in a joint portion and the pass/fail data in practical test where a joined body including the joint portion is used, and then experimentally determining, for example, allowable ranges of the properties such as the size, shape, orientation, and occurrence frequency of the defect that does not make the joined state poor.

Next, the fluororesin members (A1) and (A2) used in the first inspection method are described.

The fluororesin members (A1) and (A2) each contain a fluororesin.

The fluororesin as used herein refers to a partially crystalline fluoropolymer or fluoroplastic. The fluororesin has a melting point and has the thermoplasticity. It may be melt-fabricable or non melt-processible.

The term "melt-fabricable" as used herein means that the polymer can be melted and processed using a conventional processing device such as an extruder and an injection molding machine. A melt-fabricable fluororesin therefore normally has a melt flow rate of 0.01 to 100 g/10 min as measured by a method in conformity with ASTM D-1238 and D-2116 at a temperature higher than the crystallization melting point.

The term "non melt-processible" as used herein means that the polymer cannot be melted and processed using a conventional processing device such as an extruder and an injection molding machine. More specifically, the term "non melt-processible" means a property that the melt flow rate is not measurable at a temperature higher than the crystallization melting point by a method in conformity with ASTM D-1238 and D-2116.

In a preferred embodiment, at least one of the fluororesin members (A1) and (A2) includes a molded article containing a fluororesin.

The fluororesin contained in the molded article preferably has a melting point of 100° C. to 360° C., more preferably 140° C. to 350° C., still more preferably 160° C. to 350° C., particularly preferably 180° C. to 350° C.

The melting point of the fluororesin as used herein is the temperature corresponding to the maximum value on a heat-of-fusion curve determined by increasing the temperature at a rate of 10° C./min using a differential scanning calorimeter (DSC).

Examples of the fluororesin usable for the molded article include polytetrafluoroethylene (PTFE), a tetrafluoroethylene (TFE)/perfluoro(alkyl vinyl ether) (PAVE) copolymer (PFA), a TFE/hexafluoropropylene (HFP) copolymer (FEP), an ethylene (Et)/TFE copolymer (ETFE), a TFE/vinylidene fluoride (VDF) copolymer, an Et/TFE/HFP copolymer, polychlorotrifluoroethylene (PCTFE), a chlorotrifluoroethylene (CTFE)/TFE copolymer, an Et/CTFE copolymer, polyvinylidene fluoride (PVDF), and polyvinyl fluoride (PVF).

The fluororesin contained in the molded article is preferably at least one selected from the group consisting of PTFE and PFA, more preferably PTFE.

The PTFE may be homo PTFE consisting only of a TFE unit or modified PTFE including a TFE unit and a modifying monomer unit based on a modifying monomer copolymerizable with TFE. Modified PTFE is preferred. The PTFE is preferably high-molecular-weight, non melt-processible, fibrillatable PTFE.

The modifying monomer may be any modifying monomer copolymerizable with TFE. Examples thereof include: perfluoroolefins such as hexafluoropropylene (HFP); chlorofluoroolefins such as chlorotrifluoroethylene (CTFE); hydrogen-containing fluoroolefins such as trifluoroethylene and vinylidene fluoride (VDF); perfluorovinyl ethers; perfluoroalkylethylenes; ethylene; and fluorine-containing vinyl ethers containing a nitrile group. One modifying monomer or multiple modifying monomers may be used.

Any perfluorovinyl ether may be used. Examples include a unsaturated perfluoro compound represented by the following formula (1):

$$CF_2=CF-ORf^1 \qquad (1)$$

(wherein $Rf^1$ represents a perfluoro organic group.) The "perfluoro organic group" as used herein refers to an organic group obtained by replacing all hydrogen atoms bonded to carbon atoms with fluorine atoms. The perfluoro organic group may contain ether oxygen.

Examples of the perfluorovinyl ethers include perfluoro (alkyl vinyl ether) (PAVE) represented by the above formula (1) wherein $Rf^1$ represents a C1-C10 perfluoroalkyl group. The carbon number of the perfluoroalkyl group is preferably 1 to 5.

Examples of the perfluoroalkyl group in the PAVE include a perfluoromethyl group, a perfluoroethyl group, a perfluoropropyl group, a perfluorobutyl group, a perfluoropentyl group, and a perfluorohexyl group. Preferred is perfluoropropyl vinyl ether (PPVE) in which the perfluoroalkyl group is a perfluoropropyl group.

Examples of the perfluorovinyl ethers further include one represented by the formula (1) wherein $Rf^1$ is a C4-C9 perfluoro(alkoxyalkyl) group, one represented by the formula (1) wherein $Rf^1$ is a group represented by the following formula:

[Chem. 1]

wherein m represents 0 or an integer of 1 to 4, and one represented by the formula (1) wherein $Rf^1$ is a group represented by the following formula:

[Chem. 2]

wherein n is an integer of 1 to 4.

Any perfluoroalkylethylene may be used. Examples include perfluorobutylethylene (PFBE) and perfluorohexylethylene.

The fluorine-containing vinyl ether containing a nitrile group is more preferably a fluorine-containing vinyl ether represented by $CF_2=CFORf^2CN$ (wherein $Rf^2$ represents a C2-C7 alkylene group in which an oxygen atom is optionally inserted between two carbon atoms).

The modifying monomer for the modified PTFE is preferably at least one selected from the group consisting of PAVE and HFP, more preferably PAVE.

The modified PTFE preferably contains 0.0001 to 1% by mass of a modifying monomer unit. The lower limit of the amount of the modifying monomer unit is more preferably 0.001% by mass, still more preferably 0.01% by mass, particularly preferably 0.05% by mass. The upper limit of the amount of the modifying monomer unit is more preferably 0.5% by mass, still more preferably 0.3% by mass.

The amounts of the monomer units constituting the fluororesin herein can be calculated by appropriate combination of NMR, FT-IR, elemental analysis, and X-ray fluorescence analysis in accordance with the types of the monomers.

The PTFE preferably has a standard specific gravity (SSG) of 2.140 or greater, more preferably greater than 2.150, still more preferably 2.160 or greater, while preferably 2.210 or smaller.

The standard specific gravity (SSG) can be measured by a water displacement method in conformity with ASTM D 4895-89.

The PTFE preferably has a melting point of 324° C. to 350° C., more preferably 327° C. to 347° C. The melting point is the temperature corresponding to the maximum value on a melting curve obtained by heating a PTFE that has never been heated up to a temperature of 300° C. or higher at a rate of 10° C./min using a differential scanning calorimeter, with the curve including at least one endothermic peak within a range of 324° C. to 347° C.

Examples of the PAVE in the PFA include those represented by the above formula (1). Preferred among these are perfluoro(methyl vinyl ether) (PMVE), perfluoro(ethyl vinyl ether) (PEVE), and perfluoro(propyl vinyl ether) (PPVE).

The PFA is preferably, but is not limited to, a copolymer having a ratio by mole of a TFE unit and a PAVE unit (TFE unit/PAVE unit) of 70/30 or higher and lower than 99.5/0.5. The ratio by mole is more preferably 70/30 or higher and 98.9/1.1 or lower, still more preferably 80/20 or higher and 98.5/1.5 or lower. The PFA may be a copolymer consisting of TFE and PAVE, or may be preferably a copolymer containing a monomer unit derived from a monomer copolymerizable with TFE and PAVE in an amount of 0.1 to 10 mol % as well as a TFE unit and a PAVE unit in a total amount of 90 to 99.9 mol %. Examples of the monomer copolymerizable with TFE and PAVE include HFP, a vinyl monomer represented by $CZ^1Z^2=CZ^3(CF_2)nZ^4$ (wherein $Z^1$, $Z^2$, and $Z^3$ are the same as or different from each other, and are each a hydrogen atom or a fluorine atom; $Z^4$ is a hydrogen atom, a fluorine atom, or a chlorine atom; and n is an integer of 2 to 10), and an alkyl perfluoro vinyl ether derivative represented by $CF_2=CF-OCH_2-Rf^{11}$ (wherein $Rf^{11}$ is a C1-C5 perfluoroalkyl group).

The PFA preferably has a melting point of 180° C. to 340° C., more preferably 230° C. to 330° C., still more preferably 280° C. to 320° C. The melting point is the temperature corresponding to the maximum value on a heat-of-fusion curve obtained by increasing the temperature at a rate of 10° C./min using a differential scanning calorimeter (DSC).

The PFA preferably has a melt flow rate (MFR) of 0.1 to 100 g/10 min, more preferably 0.5 to 90 g/10 min, still more preferably 1.0 to 85 g/10 min.

The molded article may have any shape such as a shape of a film, sheet, block, rod, pipe, tube, tape, or thread. Preferred is a shape of a sheet.

The molded article is preferably a sheet containing the fluororesin, more preferably a sheet containing PTFE.

Preferably, the sheet containing a fluororesin contains the PTFE and has an average specific gravity of 2.175 or greater. The average specific gravity is more preferably greater than 2.175, still more preferably 2.178 or greater, while preferably 2.210 or smaller.

The average specific gravity refers to the specific gravity of the entire sheet containing a fluororesin. In the case where the sheet containing a fluororesin is heated to include a portion (layer) in which the specific gravity is lowered, the average specific gravity refers to the specific gravity of the entire sheet including such a low specific gravity layer.

The average specific gravity of the sheet can be measured by a water displacement method. A measurement sample may have any shape or size. For example, a measurement sample is cut out of the sheet in a size of about 2 cm in length×2 cm in width.

The sheet containing the PTFE and having an average specific gravity of 2.175 or greater contains high crystalline PTFE, and therefore has excellently low chemical permeability. Such a high crystalline PTFE sheet can be obtained, for example, by the method disclosed in PCT/JP98/01116, specifically by cutting a fired product obtained by a rotary firing method, in which a PTFE compact made of PTFE powder is fired while being rotated, into a sheet.

The thickness of the sheet containing a fluororesin varies in accordance with the intended use, and is normally 1 to 4 mm. In the case of using the sheet for a backing sheet, the thickness is about 2 to 4 mm.

The molded article is also preferably a laminate including the sheet containing a fluororesin and a heat-resistant fiber layer, more preferably a laminate including a sheet containing PTFE and a heat-resistant fiber layer.

Examples of a heat-resistant fiber contained in the heat-resistant fiber layer include glass fiber, carbon fiber, polyamide imide fiber, and boron nitride fiber. Preferred among these are glass fiber and carbon fiber.

The heat-resistant fiber layer preferably includes a fabric of the heat-resistant fiber, more preferably a woven fabric of the heat-resistant fiber.

The heat-resistant fiber layer preferably includes at least one selected from the group consisting of a glass cloth and a carbon cloth, more preferably a glass cloth.

The glass cloth is preferably a woven fabric of glass yarn. The glass yarn may be a bulked glass yarn or a glass yarn without bulking (straight yarn). In order to obtain a glass cloth excellent in adhesion to the sheet containing a fluororesin (and to a hot-melt resin layer described later) and flexibility, the glass yarn is preferably a bulked glass yarn.

The bulking is one of techniques for increasing the volume of fibers and is also called texturing. In the case of glass yarns, the bulking is performed by supplying a glass yarn into a high-speed air jet nozzle at a certain drawing rate and exposing the glass yarn to a turbulent flow of the air at a winding rate lower than the drawing rate to cause opening of the glass yarn.

The bulked glass yarn preferably includes intertwined glass filaments. The glass filaments preferably have an average diameter of 2 to 10 µm, more preferably 4 to 7 µm. The number of glass filaments intertwined together is preferably 200 to 6000, more preferably 400 to 2400. Examples of the glass yarn used include yarns of D-glass, DE-glass, E-glass, G-glass, or the like generally known as the nominal diameters (symbols) of glass staple fibers.

The bulked glass yarn may be used in the form of a single yarn or of a doubled and twisted yarn of multiple yarns intertwined.

The bulked glass yarn preferably has a count (yarn weight) of 30 to 200 tex, more preferably 50 to 100 tex.

In order to firmly bond the glass cloth and the hot-melt resin layer, the bulked glass yarn preferably has a bulking percentage of 101% or higher, more preferably 103% or higher, still more preferably 105% or higher. The upper limit of the bulking percentage may be, but not limited to, 200%. In processing of the glass yarn into a fabric, the upper limit of the bulking percentage is preferably 150%, more preferably 130%, still more preferably 120%.

The bulking percentage is a value determined by the ratio of the count (yarn weight) of the bulked glass yarn and the count (yarn weight) of the glass yarn before bulking.

The count (yarn weight) of the bulked glass yarn is the mass of the glass yarn per unit length. The count (yarn weight) of the glass yarn before bulking is the mass determined from the thickness of the glass filaments and the total number of the filaments.

The fabric may be either a woven fabric or a knitted fabric, and is produced by weaving or knitting the glass yarn. Examples of methods of weaving or knitting the glass yarn include known methods using a weaving or knitting machine. Specific examples thereof include weaving of glass fibers using a jet loom (e.g., an air jet loom or a water jet loom), a Sulzer loom, or a rapier loom. Examples of weaving methods (weaving patterns) for a woven fabric after warping and sizing of a glass yarn include plain weave, satin weave, mat weave, twill weave, leno weave, triaxial weave, and horizontal stripe weave. Examples of knitting methods (knitting patterns) for a knitted fabric include weft knit such as plain stitch, rib stitch, and purl stitch, warp knit such as single denbigh stitch, single cord stitch, and two needle stitch, lace stitch, float stitch, and pile stitch. The knitting may be performed using a known weft knitting machine or warp knitting machine, such as a latch needle plain fabric circular knitting machine, a circular knitting machine, or a cotton's patent knitting machine. Preferred among these is a woven fabric in a twill pattern.

The glass cloth preferably includes a warp and a weft. In the case of using the bulked glass yarn, the bulked glass yarn is preferably used for at least one selected from the warp and the weft. More preferably, the bulked glass yarn is used for one selected from the warp and the weft, while a non-bulked glass yarn is used for the other. Contact between the surface with the bulked glass yarn appearing thereon and the sheet containing a fluororesin of the laminate allows the glass cloth and the sheet containing a fluororesin to firmly bond to each other. Further, use of the bulked glass yarn for at least one selected from the warp and the weft allows the glass cloth to have much better flexibility and thus to be much less likely to break when the laminate is bent.

In the case where the glass cloth includes the bulked glass yarn and non-bulked glass yarn, the bulked glass yarn and the non-bulked glass yarn preferably give a mass ratio of 100/0 to 10/90, more preferably 100/0 to 40/60.

The glass cloth may have a thickness selected in accordance with the intended use, and may be 0.03 to 3.0 mm, for example. In the case of using the glass cloth for a backing sheet, the thickness is preferably 0.1 to 0.5 mm.

The laminate preferably further includes a hot-melt resin layer. The hot-melt resin can melt during thermal bonding and impregnate into the heat-resistant fiber layer. Thus, the hot-melt resin layer firmly bonds to the heat-resistant fiber layer. The hot-melt resin layer is also excellent in adhesion to the sheet containing a fluororesin. Thus, the hot-melt resin layer can firmly bond the sheet containing a fluororesin and the heat-resistant fiber layer with the hot-melt resin layer in between.

The hot-melt resin layer used is a film or sheet of a hot-melt resin. The hot-melt resin may be any resin that can thermally adhere to the sheet containing a fluororesin. Examples thereof include olefinic resins having a melting point close to the melting point of the fluororesin; aromatic resins such as PPS, PES, and PEEK; and hot-melt fluororesins such as a TFE-PAVE copolymer (PFA) and a TFE-hexafluoropropylene copolymer (FEP). Preferred among these are hot-melt fluororesins because they have properties similar to those of the fluororesin and good adhesion to the fluororesin. Particularly, preferred for use in a backing sheet are PFA and FEP, and more preferred is PFA.

The hot-melt resin layer has a thickness appropriately selected in accordance with the intended use. In the case of using the hot-melt resin layer as an adhesive layer between the sheet containing a fluororesin and the heat-resistant fiber layer in a backing sheet, for example, the thickness may be about 10 to 300 µm.

The sheet containing a fluororesin, the hot-melt resin layer, and the heat-resistant fiber layer are preferably laminated in the stated order. In other words, preferably, the sheet containing a fluororesin and the heat-resistant fiber layer are bonded to each other with the hot-melt resin layer in between. The hot-melt resin layer is excellent in both adhesion to the sheet containing a fluororesin and adhesion to the heat-resistant fiber layer. Thus, the above laminating order can provide a laminate in which the sheet containing a fluororesin and the hot-melt resin layer are firmly bonded to each other and the hot-melt resin layer and the heat-resistant fiber layer are firmly bonded to each other. According to the intended use, a layer of non-fired PTFE fine particles may be provided between the sheet containing a fluororesin and the hot-melt resin layer. In the case of providing a layer of non-fired PTFE fine particles, the non-fired PTFE preferably has a melting energy (heat of fusion) of 65 J/g or lower. The melting energy (heat of fusion) is the melting energy (heat of fusion) within 290° C. to 350° C. calculated from a melting curve obtained by heating a PTFE that has never been heated up to a temperature of 300° C. or higher at a rate of 10° C./min using a differential scanning calorimeter (DSC), with the curve including at least one endothermic peak within a range of 324° C. to 347° C.

It should be noted that the absence of the layer of PTFE fine particles does not cause any disadvantage in the case where the sheet containing a fluororesin and the heat-resistant fiber layer are sufficiently firmly bonded to each other.

In the laminate, more preferably, the sheet containing a fluororesin, the hot-melt resin layer, and the heat-resistant fiber layer are laminated in the stated order, the sheet containing a fluororesin and the hot-melt resin layer are directly bonded to each other, and the hot-melt resin layer and the heat-resistant fiber layer are directly bonded to each other.

In the case of laminating the layers such that the hot-melt resin layer and the heat-resistant fiber layer are in contact with each other, a layer of the heat-resistant fiber impregnated with the hot-melt resin is preferably formed on the surface in contact with the hot-melt resin layer of the heat-resistant fiber layer. Such a structure allows the heat-resistant fiber layer and the hot-melt resin layer to be more firmly bonded to each other. The layer impregnated with the hot-melt resin is formed, for example, by impregnation of the heat-resistant fiber with the hot-melt resin in a molten state during thermal bonding and subsequent solidification thereof.

In the case where the heat-resistant fiber layer used is a glass cloth that is a fabric of bulked glass yarn, the bulked glass yarn preferably appears on a surface in contact with the hot-melt resin layer of the glass cloth. More preferably, a layer of the bulked glass yarn impregnated with the hot-melt resin is formed on the contact surface. Still more preferably, a layer impregnated with the hot-melt resin is formed between strands of the bulked glass yarn and between glass filaments constituting the bulked glass yarn on the contact surface. These structures allow the glass cloth and the hot-melt resin layer to be more firmly bonded to each other. The layer impregnated with the hot-melt resin is formed, for example, by impregnation of the strands of the glass yarn (and the glass filaments) with the hot-melt resin in a molten state during thermal bonding and subsequent solidification thereof.

In a particularly preferred embodiment of the laminate, the layers are laminated such that the hot-melt resin layer and the glass cloth are in contact with each other, the glass cloth is woven in a twill pattern, and the bulked glass yarn is used for at least one selected from the warp and the weft of the glass cloth and appears on a surface in contact with the hot-melt resin layer of the glass cloth.

In another particularly preferred embodiment of the laminate, the bulked glass yarn includes intertwined glass filaments, and the glass cloth includes, on a surface in contact with the hot-melt resin layer, a layer of the bulked glass yarn and the glass filaments impregnated with the hot-melt resin.

Before lamination, the sheet containing a fluororesin may be subjected to heat treatment. The heat treatment can planarize the sheet containing a fluororesin to facilitate lamination with other layers.

The temperature of the heat treatment is preferably 100° C. to 320° C.

The duration of the heat treatment is preferably 1 to 30 minutes.

The laminate can be produced by a method including stacking and thermally bonding the sheet containing a fluororesin, the film or sheet of a hot-melt resin, and the woven fabric of the heat-resistant fiber.

Specific conditions employed may be, for example, the conditions described in WO 00/10805, WO 2019/082582, or the like.

In the laminate obtainable by the above production method, a fired layer and an unfired layer may be formed in the sheet containing a fluororesin. The fired layer is a layer melted during the thermal bonding and is formed in a portion close to the heat-resistant fiber layer (heating side) in the sheet containing a fluororesin. The unfired layer is a layer not melted during the thermal bonding. Normally, the fired layer is clear and the unfired layer is white and opaque.

In a preferred embodiment, one of the fluororesin members (A1) and (A2) is a joint member containing a fluororesin.

The fluororesin in the joint member preferably has a melting point of 100° C. to 360° C., more preferably 140° C. to 350° C., still more preferably 160° C. to 350° C., particularly preferably 180° C. to 320° C.

The melting point of the fluororesin is the temperature corresponding to the maximum value on a heat-of-fusion curve determined by increasing the temperature at a rate of 10° C./min using a differential scanning calorimeter (DSC).

Examples of the fluororesin usable for the joint member include polytetrafluoroethylene (PTFE), a tetrafluoroethylene (TFE)/perfluoro(alkyl vinyl ether) (PAVE) copolymer (PFA), a TFE/hexafluoropropylene (HFP) copolymer (FEP), an ethylene (Et)/TFE copolymer (ETFE), a TFE/vinylidene fluoride (VDF) copolymer, an Et/TFE/HFP copolymer, polychlorotrifluoroethylene (PCTFE), a chlorotrifluoroethylene (CTFE)/TFE copolymer, an Et/CTFE copolymer, polyvinylidene fluoride (PVDF), and polyvinyl fluoride (PVF).

In particular, the fluororesin contained in the joint member is preferably at least one selected from the group consisting of modified PTFE, PFA, and FEP, more preferably at least one selected from the group consisting of PFA and FEP, still more preferably PFA.

The fluororesin contained in the joint member may be a perfluoro resin.

Preferably, the modified PTFE includes a TFE unit and a modifying monomer unit, and the amount of the modifying monomer unit is 0.05 to 0.7% by mass based on the whole monomer units. The modifying monomer is preferably at least one selected from the group consisting of PAVE and HFP.

The modified PTFE preferably has a melt viscosity of $1 \times 10^8$ to $15 \times 10^8$ Pa·s.

The melt viscosity q is measured using a dynamic viscoelastometer (product name: PDS-II, available from Rheometric Scientific).

Examples of PAVE in the PFA include those represented by the formula (1) mentioned above. Preferred among these are perfluoro(methyl vinyl ether) (PMVE), perfluoro(ethyl vinyl ether) (PEVE), and perfluoro(propyl vinyl ether) (PPVE).

The PFA is preferably, but is not limited to, a copolymer having a ratio by mole of a TFE unit and a PAVE unit (TFE unit/PAVE unit) of 70/30 or higher and lower than 99.5/0.5. The ratio by mole is more preferably 70/30 or higher and 98.9/1.1 or lower, still more preferably 80/20 or higher and 98.5/1.5 or lower. The PFA may be a copolymer consisting of TFE and PAVE, or may be preferably a copolymer containing a monomer unit derived from a monomer copolymerizable with TFE and PAVE in an amount of 0.1 to 10 mol % as well as a TFE unit and a PAVE unit in a total amount of 90 to 99.9 mol %. Examples of the monomer copolymerizable with TFE and PAVE include HFP, a vinyl monomer represented by $CZ^1Z^2=CZ^3(CF_2)nZ^4$ (wherein $Z^1$, $Z^2$, and $Z^3$ are the same as or different from each other, and are each a hydrogen atom or a fluorine atom; $Z^4$ is a hydrogen atom, a fluorine atom, or a chlorine atom; and n is an integer of 2 to 10), and an alkyl perfluoro vinyl ether derivative represented by $CF_2=CF-OCH_2-Rf^{11}$ (wherein $Rf^{11}$ is a C1-C5 perfluoroalkyl group).

The PFA preferably has a melting point of 180° C. to 340° C., more preferably 230° C. to 330° C., still more preferably 280° C. to 320° C. The melting point is the temperature corresponding to the maximum value on a heat-of-fusion curve obtained by increasing the temperature at a rate of 10° C./min using a differential scanning calorimeter (DSC).

The PFA preferably has a melt flow rate (MFR) of 0.1 to 100 g/10 min, more preferably 0.5 to 90 g/10 min, still more preferably 1.0 to 85 g/10 min.

The FEP is preferably, but is not limited to, a copolymer having a ratio by mole of a TFE unit and a HFP unit (TFE unit/HFP unit) of 70/30 or higher and lower than 99/1. The ratio by mole is more preferably 70/30 or higher and 98.9/1.1 or lower, still more preferably 80/20 or higher and 97/3 or lower. The FEP is also preferably a copolymer containing a monomer unit derived from a monomer copolymerizable with TFE and HFP in an amount of 0.1 to 10 mol %, as well as a TFE unit and a HFP unit in a total amount of 90 to 99.9 mol %. Examples of the monomer copolymerizable with TFE and HFP include PAVE and an alkyl perfluoro vinyl ether derivative.

The FEP preferably has a melting point of 150° C. to 320° C., more preferably 200° C. to 300° C., still more preferably 240° C. to 280° C. The melting point is the temperature corresponding to the maximum value on a heat-of-fusion curve determined by increasing the temperature at a rate of 10° C./min using a differential scanning calorimeter (DSC).

The FEP preferably has a MFR of 0.01 to 100 g/10 min, more preferably 0.1 to 80 g/10 min, still more preferably 1 to 60 g/10 min, particularly preferably 1 to 50 g/10 min.

The amounts of the monomer units constituting the fluororesin herein can be calculated by appropriate combination of NMR, FT-IR, elemental analysis, and X-ray fluorescence analysis in accordance with the types of the monomers.

The fluororesin members may be joined using the joint member containing a fluororesin by any conventionally known method. For example, a method in conformity with the method described in JP 2004-189939 A is employable.

The first inspection method enables easy inspection of an internal condition of a joint portion between fluororesin members, and therefore is useful for, for example, adjustment of the joining (welding) conditions. The first inspection method also enables non-destructive inspection of an internal condition of a joint portion between fluororesin members at high speed, and thus can be used for applications such as determination of the quality (pass/fail) of the joining condition at a working site where fluororesin members are joined.

The first inspection method can be suitably used for inspection of a joint portion between backing sheets in use of backing sheets for lining various containers, tanks, piping, and the like.

The disclosure also relates to a method for inspecting a fluororesin member, including: a step (B1) of inspecting an internal condition of a fluororesin member (B1) based on image data obtained by imaging the fluororesin member (B1) by optical coherence tomography (OCT) (hereafter, also referred to as a second inspection method).

The second inspection method enables non-destructive inspection of an internal condition of a fluororesin member, and thus enables inspection of all fluororesin members. This can therefore improve the reliability of the quality of the fluororesin member.

The second inspection method enables precise analysis based on the obtained image data, and thus enables detection of defects including minor internal defects and digitalization of the condition of a lamination interface in the case where the member is a laminate. This enables exact understanding of the internal condition of the fluororesin member, allowing determination of an objective index for examining the quality of the fluororesin member. Thus, the quality of the fluororesin member can be stabilized.

OCT imaging can be performed at high speed, and thus the inspection method can be easily introduced into a production site of the fluororesin member. This enables improvement and stabilization of the quality of the fluororesin member without greatly increasing the number of steps carried out at the production site.

In the step (B1), the fluororesin member (B1) is to be inspected. The fluororesin member (B1) is a member containing a fluororesin.

The fluororesin member (B1) may be either a molded article or a joint member, preferably a molded article.

According to a preferred embodiment, the fluororesin member (B1) is a sheet containing a fluororesin.

According to another preferred embodiment, the fluororesin member (B1) is a laminate including a sheet containing a fluororesin and a heat-resistant fiber layer.

The fluororesin contained in the fluororesin member (B1), the molded article, the joint member, the sheet, and the laminate may be the same as those having been described for the fluororesin members (A1) and (A2).

The inspection in the step (B1) is performed based on image data obtained by imaging the fluororesin member (B1) by OCT. The second inspection method may include a step of imaging the member by OCT to obtain image data based on the member.

The types of OCT and light, an OCT device, and a basic imaging method employable in the step (B1) may be the same as those having been described for the step (A1).

In the OCT imaging in the step (B1), the light from the light source of an OCT device preferably has an incident angle $\alpha$ of 3 to 30 degrees relative to the member. The incident angle $\alpha$ is more preferably 5 degrees or greater, still more preferably 7 degrees or greater, while more preferably 30 degrees or smaller, still more preferably 20 degrees or smaller, further more preferably 15 degrees or smaller, particularly preferably 10 degrees or smaller.

Setting the incident angle $\alpha$ within the above range can reduce noise in the image and can clarify a signal due to a defect of the member.

The above effects are significant when the member has a high near-infrared transmittance and when the front surface (surface close to the OCT light source) and back surface (surface opposite to the front surface) to be inspected of the member are parallel to each other.

The definition and the adjusting method of the incident angle $\alpha$ are as described above in the step (A1).

In the OCT imaging in the step (B1), the light incident on the member preferably has an intensity of 1 mW to 18 mW. The intensity of the light is more preferably 5 mW or higher, still more preferably 10 mW or higher, while more preferably 15 mW or lower, still more preferably 12 mW or lower.

Setting the intensity of the light within the above range can reduce noise in the image and can clarify a signal due to a defect of the member.

The above effect is significant when the member has a high near-infrared transmittance and when the front surface and back surface of the member are parallel to each other.

In the description, the intensity of light incident on the member is the intensity of light at a probe end of an OCT device.

When a portion to be inspected in the sample is close to a sample stage, the system is preferably devised so that the light passed through the sample does not affect the inspection by the same method as the method having been described for the step (A1).

In the step (B1), an internal condition of the fluororesin member (B1) is inspected based on the image data.

The inspection may be performed using an image obtained from the image data or may be performed by processing the image data, or both may be used in combination.

In the case where the fluororesin member (B1) is the laminate, in the step (B1), a condition of the interface between the sheet containing a fluororesin and the heat-resistant fiber layer is preferably inspected.

When the fluororesin member (B1) is the laminate, there may be a case where a fired layer and an unfired layer are formed in the sheet containing a fluororesin as described later. The above inspection can determine the presence or absence of the fired layer and the unfired layer and the thickness of the layers, if present.

In the case where the laminate further includes a hot-melt resin layer described later, the above inspection can determine the presence or absence of a layer made of the heat-resistant fibers impregnated with a hot-melt resin and the thickness of the layer, if present.

The inspection is preferably inspection of a defect inside the member.

Examples of the defect include cracking, delamination, voids, and foreign substances. Embodiments of the defect include the absence of a layer which should be present and the thickness of a layer not within a required range. The defect may be caused by molding failure.

When the fluororesin member (B1) is a laminate, the interface between different materials is likely to suffer denaturation or have voids, causing a defect.

The inspection preferably determines the presence or absence of a defect.

The step (B1) is preferably a step of inspecting a defect inside the member based on the image data, more preferably a step of inspecting cracking and delamination inside the member based on the image data.

The inspection may be performed based on a signal due to a defect inside the member in the image data. Further, the presence or absence of a defect is preferably determined based on a signal due to the defect.

An example of a method for determining the presence or absence of the defect may be a method in which the cases where no signal due to any of the aforementioned defects is observed in the image obtained by OCT are determined as the absence of a defect, while the cases where a signal due to at least one of the aforementioned defects is observed in the image are determined as the presence of a defect.

If the inspection determines the presence of a defect, the size, shape, orientation, occurrence frequency, and other properties of the defect may be further analyzed. Such analysis enables easy determination of whether or not the above defect is a defect that causes the member to be determined as defective. The analysis may be performed, for example, by processing a signal due to the defect.

The second inspection method may further include a step (B2) of determining whether the fluororesin member (B1) is a good product or not based on a result of the inspection in the step (B1).

For example, the step (B2) may be a step of determining a member as a good product when the member has been determined as having no defect in the step (B1), while determining a member as a defective product when the member has been determined as having a defect in the step (B1).

Alternatively, the step (B2) may be a step of determining, as good products, a member that has been determined as having no defect in the step (B1) and a member that has been determined as having a defect in the step (B1) and that has a defect whose degree is not higher than a predetermined standard, while determining, as a defective product, a member having a defect whose degree is higher than the predetermined standard among the members that have been determined as having a defect.

The standard for the degree of a defect may be determined as appropriate with no limitation in accordance with, for example, the required characteristics of a member. For example, the standard may be determined by obtaining in advance a correlation between the properties such as the size, shape, orientation, and occurrence frequency of a defect in a member and the pass/fail data in practical test where the member is used as a part, and then experimentally determining, for example, allowable ranges of the properties such as the size, shape, orientation, and occurrence frequency of the defect that does not cause the member to be determined as a defective product.

The second inspection method enables easy inspection of an internal condition of a member, and therefore is useful for adjustment of the molding conditions and lamination conditions. The second inspection method also enables non-destructive inspection of an internal condition of a member at high speed, and thus can be used for applications such as sorting of good products and defective products in production of members and acceptance inspection of members.

The second inspection method can be favorably used for inspection of internal conditions of a fluororesin member before joining and a sheet containing a fluororesin before lamination. In particular, the second inspection method can be favorably used for inspection of a sheet containing a fluororesin as a material (raw fabric sheet) in production of a backing sheet for lining of various containers, tanks, and piping and for inspection of the resulting backing sheet (laminate).

The second inspection method can be also favorably used for inspection of an internal condition of a portion other than the joint portion in a joined body of fluororesin members.

The disclosure relates to a method for inspecting a joint portion between fluororesin members, including: a step (A1) of inspecting an internal condition of a joint portion between a fluororesin member (A1) and a fluororesin member (A2) based on image data obtained by imaging the joint portion by optical coherence tomography.

Preferably, at least one of the fluororesin members (A1) and (A2) includes a sheet containing a fluororesin.

Preferably, at least one of the fluororesin members (A1) and (A2) includes a laminate that includes a sheet containing a fluororesin and a heat-resistant fiber layer.

The disclosure also relates to a method for inspecting a fluororesin member, including: a step (B1) of inspecting an internal condition of a fluororesin member (B1) based on image data obtained by imaging the fluororesin member (B1) by optical coherence tomography.

Preferably, the fluororesin member (B1) includes a sheet containing a fluororesin.

Preferably, the fluororesin member (B1) includes a laminate that includes a sheet containing a fluororesin and a heat-resistant fiber layer.

EXAMPLES

The disclosure will be described in more detail with reference to examples, but the disclosure is not limited to these examples.

Example 1

On a PTFE sheet (melting point: 328° C.) having a thickness of 1 mm, a length of 90 mm, and a width of 20 mm was stacked a PFA sheet (melting point: 304° C.) having a thickness of 1 mm, a length of 60 mm, and a width of 10 mm. They are heat-treated at 320° C. at atmospheric pressure for five minutes with a tong hold for a peeling test left. Thus, a sample was obtained.

Figure 5:
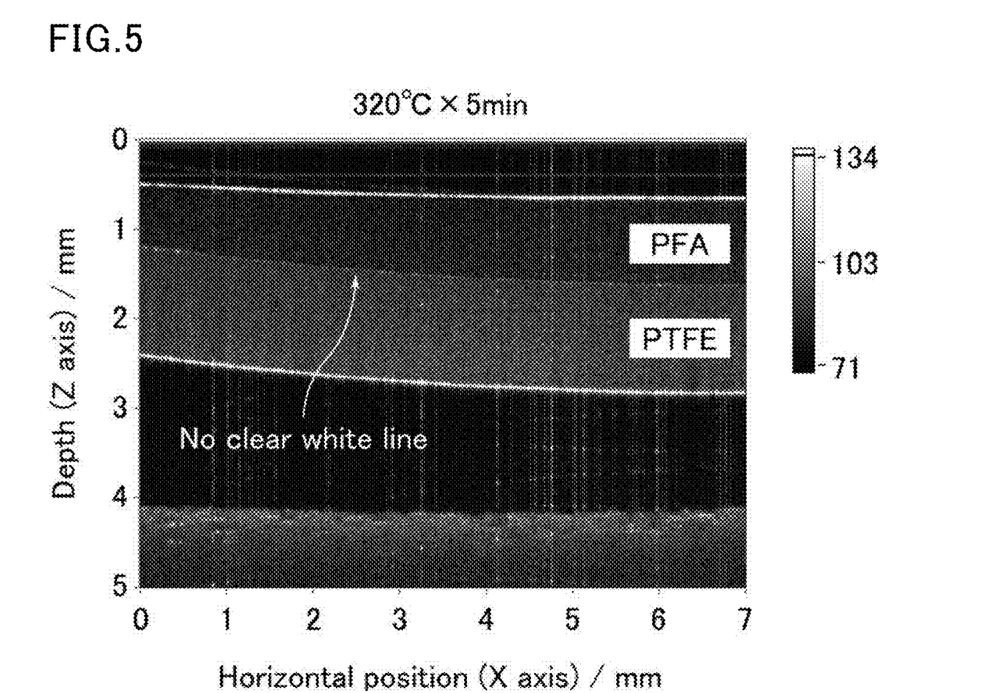
FIG. 5 is an OCT image obtained in Example 1.

A heat-treated portion of the sample was subjected to OCT imaging under the following conditions. FIG. 5 shows the obtained OCT image. In the OCT image, no clear white line was observed at the interface between PTFE and PFA.

According to a T-peel test by the following method, the sample had a peel strength of 17 N/10 mm.

<OCT Imaging>
OCT device: SweptSys-02 (available from Systems Engineering Inc.)
Swept laser light source for OCT: center wavelength of 1310 nm, spectrum width of 100 nm, scan rate of 50 kHz, coherence length of 12 mm, optical output power of 18 mW (13 mW at probe end)
Imaging conditions: luminance of 100, contrast of 30

<T-Peel Test>
Using a tensile tester (TENSILON, available from Orientec Co., Ltd.), a T-peel test was performed at a peel rate of 20 mm/min at 25° C. to determine the peel strength (maximum value).

Example 2

A sample was obtained as in Example 1, except that the heat treatment temperature was changed to 310° C.

Figure 6:
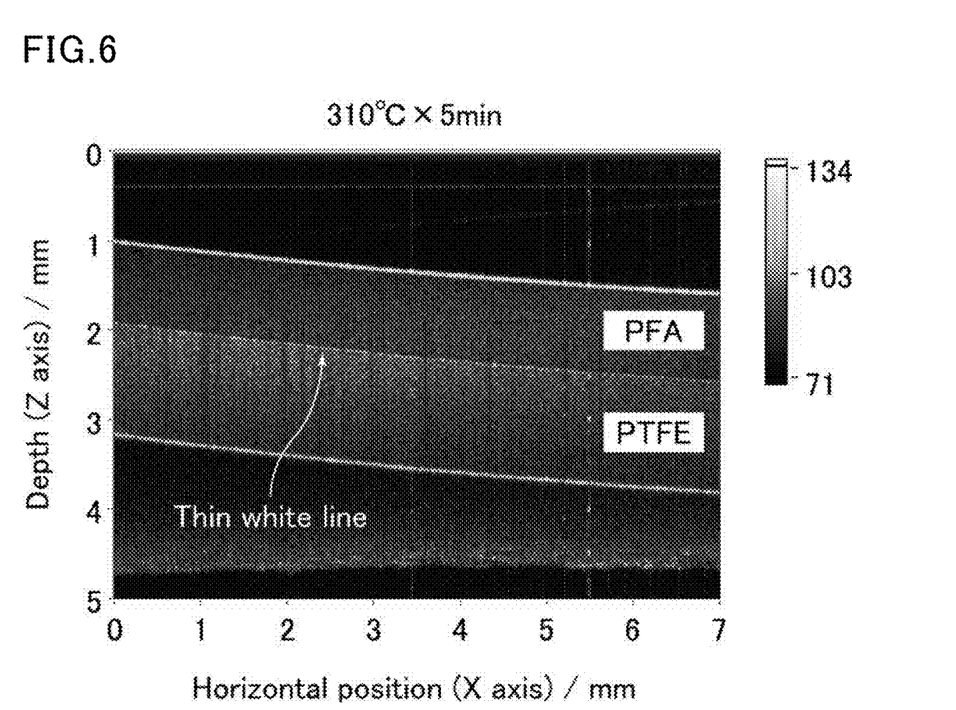
FIG. 6 is an OCT image obtained in Example 2.

A heat-treated portion of the sample was subjected to OCT imaging as in Example 1. FIG. 6 shows the obtained OCT image. In the OCT image, a thin white line was observed at the interface between PTFE and PFA.

According to the T-peel test carried out as in Example 1, the sample had a peel strength of 1 N/10 mm.

Example 3

A sample was obtained as in Example 1, except that the heat treatment temperature was changed to 300° C.

Figure 7:
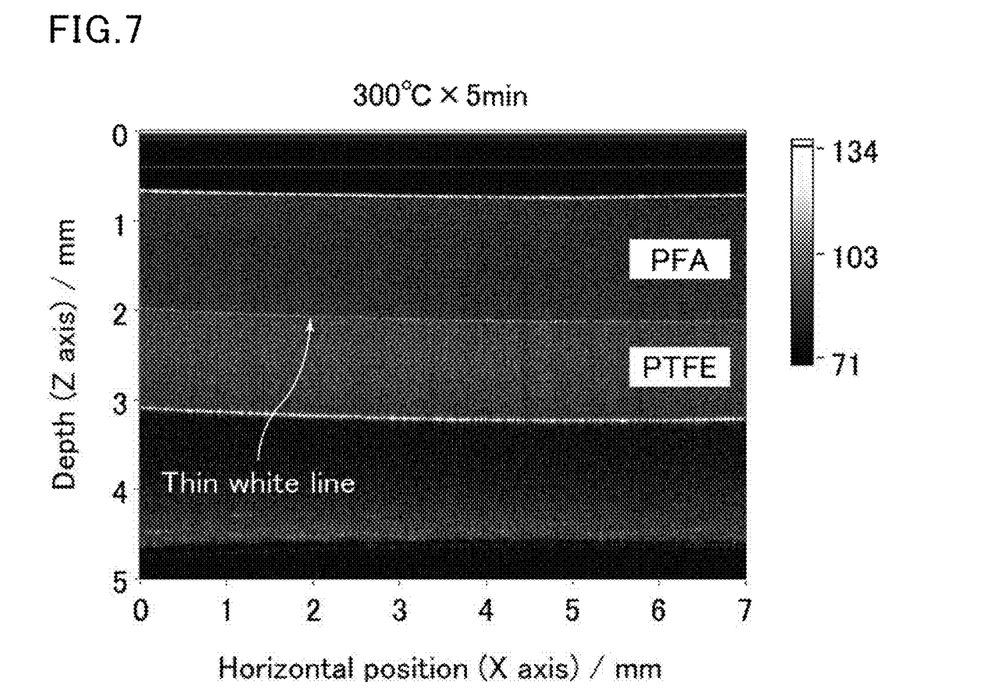
FIG. 7 is an OCT image obtained in Example 3.

A heat-treated portion of the sample was subjected to OCT imaging as in Example 1. FIG. 7 shows the obtained OCT image. In the OCT image, a thin white line was observed at the interface between PTFE and PFA.

According to the T-peel test carried out as in Example 1, the sample had a peel strength of 1 N/10 mm.

Example 4

A sample was obtained as in Example 1, except that the heat treatment temperature was changed to 295° C.

Figure 8:
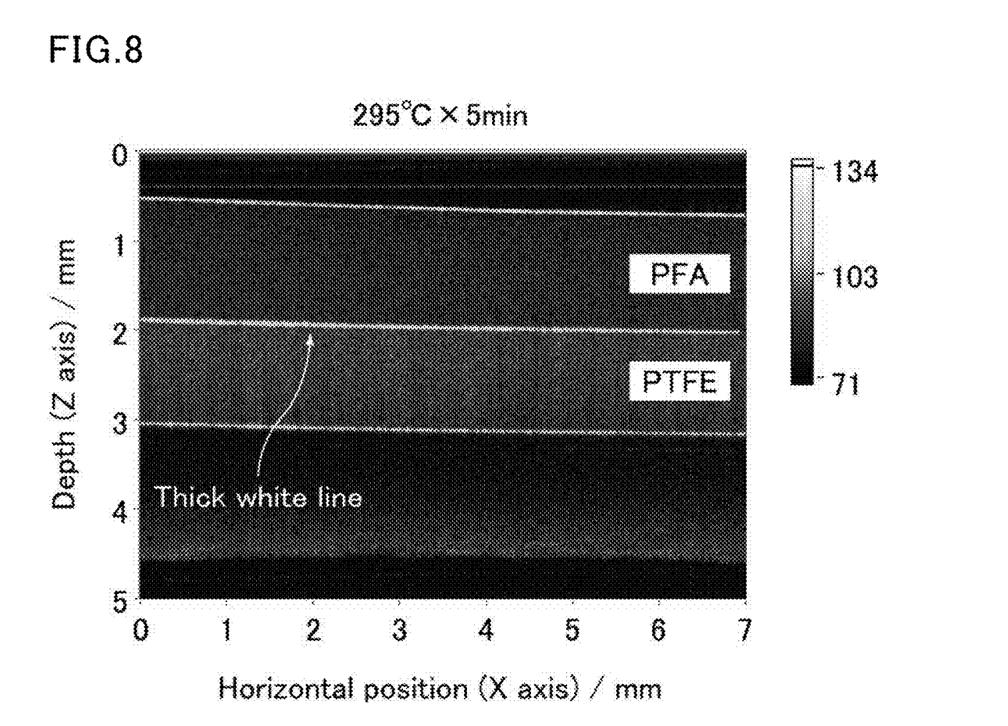
FIG. 8 is an OCT image obtained in Example 4.

A heat-treated portion of the sample was subjected to OCT imaging as in Example 1. FIG. 8 shows the obtained OCT image. In the OCT image, a thick white line was observed at the interface between PTFE and PFA.

The T-peel test was tried to be performed using the sample as in Example 1, but PTFE and PFA were separated from each other upon setting the sample on the tester.

According to the results in Examples 1 to 4, PTFE and PFA were firmly bonded to each other when no clear white line was observed at their interface in the OCT image, while PTFE and PFA were not or insufficiently bonded to each other when a white line was observed at the interface in the OCT image.

The PTFE sheets and PFA sheets used in Example 1 to 4 were confirmed not to have a defect of 10 μm or larger such as cracking, delamination, and voids, and other defects including foreign substances, the absence of a layer which should be present, and the thickness of a layer not within a required range.

REFERENCE SIGNS LIST

1, 2: sheet containing a fluororesin
3, 4: sheet containing a fluororesin
5: joint member containing a fluororesin
6, 7: laminate
6a, 7a: sheet containing a fluororesin
6b, 7b: heat-resistant fiber layer
10: OCT device
11: light source
12: beam splitter
13: reference mirror
14: light detector
15: sample

What is claimed is:

1. A method for inspecting a joint portion between fluororesin members, comprising:
   a step (A1) of inspecting cracking and delamination inside a joint portion between a fluororesin member (A1) and a fluororesin member (A2) based on image data obtained by imaging the joint portion by optical coherence tomography (OCT) using light having a center wavelength of 1100±50 nm, 1320±50 nm, or 1750±100 nm,
   wherein whether the fluororesin members (A1) and (A2) are firmly bonded to each other at the joint portion is determined based on whether a clear white line is observed at their interface in the OCT image.

2. The inspection method according to claim 1,
   wherein at least one of the fluororesin members (A1) and (A2) comprises a sheet containing a fluororesin.

3. The inspection method according to claim 1,
   wherein at least one of the fluororesin members (A1) and (A2) comprises a laminate that includes a sheet containing a fluororesin and a heat-resistant fiber layer.

4. A method for inspecting a fluororesin member, comprising:
   a step (B1) of inspecting cracking and delamination inside a fluororesin member (B1) based on image data obtained by imaging the fluororesin member (B1) by optical coherence tomography (OCT) using light having a center wavelength of 1100±50 nm, 1320±50 nm, or 1750=100 nm,
   wherein the fluororesin member (B1) comprises a laminate that includes a PTFE sheet having an average specific gravity of ≥2.175 and a heat-resistant fiber layer,
   wherein whether the PTFE sheet and the heat-resistant fiber layer are firmly bonded to each other at the joint portion is determined based on whether a clear white line is observed at their interface in the OCT image.

5. The inspection method according to claim 1, wherein (i) the fluororesin members (A1) and (A2) contain different fluororesins, and (ii) the different fluororesins are independently selected from the group consisting of PTFE and a TFE/PAVE copolymer.

6. The inspection method according to claim 1, wherein the fluororesin member (A1) consists of PTFE, and the fluororesin member (A2) consists of TFE/PAVE copolymer.

* * * * *